(12) United States Patent
Wallace

(10) Patent No.: US 7,329,247 B2
(45) Date of Patent: Feb. 12, 2008

(54) METHOD FOR TOXIN REMOVAL FROM A MAMMAL'S BREAST VIA LACTATION AND LIFELIKE LACTATION-INDUCING BABY MANNEQUIN BREAST PUMP

(76) Inventor: Gary L. Wallace, 4147 W. 9860 North, Cedar Hills, UT (US) 84062-9447

( * ) Notice: Subject to any disclaimer, the term of this patent is extended or adjusted under 35 U.S.C. 154(b) by 511 days.

(21) Appl. No.: 10/428,036

(22) Filed: May 2, 2003

(65) Prior Publication Data

US 2003/0208182 A1 Nov. 6, 2003

Related U.S. Application Data

(60) Provisional application No. 60/377,525, filed on May 3, 2002.

(51) Int. Cl.
*A61M 31/00* (2006.01)

(52) U.S. Cl. .................................................. 604/500

(58) Field of Classification Search ............ 604/73–76, 604/131, 132, 154, 118, 120, 540, 65–67, 604/500; 128/DIG. 12, DIG. 13
See application file for complete search history.

(56) References Cited

U.S. PATENT DOCUMENTS

| 5,776,098 A * | 7/1998 | Silver et al. .................. 604/74 |
| 6,440,100 B1 * | 8/2002 | Prentiss ....................... 604/74 |
| 6,517,513 B1 * | 2/2003 | Covington et al. ........... 604/74 |
| 6,547,756 B1 * | 4/2003 | Greter et al. ................. 604/74 |

* cited by examiner

*Primary Examiner*—Manuel Mendez
(74) *Attorney, Agent, or Firm*—Kirton & McConkie; Michael F. Krieger

(57) ABSTRACT

A method for inducing lactation for the purpose of removing harmful toxins from a woman's body is provided. Specifically, the present invention includes, among other methods, using a baby mannequin-breast pump to induce lactation and to enable comfortable and efficient toxin removal from a woman's breast.

3 Claims, 1 Drawing Sheet

METHOD FOR TOXIN REMOVAL FROM A MAMMAL'S BREAST VIA LACTATION AND LIFELIKE LACTATION-INDUCING BABY MANNEQUIN BREAST PUMP

RELATED APPLICATIONS

This application claims priority to provisional patent application Ser. No. 60/377,525, filed May 3, 2002, entitled "METHOD FOR TOXIN REMOVAL FROM A MAMMAL'S BREAST VIA LACTATION AND LIFE LIKE BREAST PUMP MANIKIN."

BACKGROUND OF THE INVENTION

1. Field of Invention

The present invention relates generally to a method for inducing lactation for the purpose of removing harmful toxins from a woman's body. More particularly, the present invention includes, among other methods, using a lactation-inducing breast pump to enable comfortable and efficient toxin removal from a woman's breast.

2. Background and Related Art

Women breastfeed in order to provide milk to their newborn infants. It is well proven that a mother's milk is optimal in nutrients for her infant. Not as well known, but proven in various studies, is the fact a mother also passes harmful toxins from her body to her infant's during breastfeeding. These harmful toxins include lead, dioxins, dichlorodiphenyl dichloroethane (DDT), polychlorinated biphenyls (PCBs), various drugs, and a variety of other carcinogenic and birth defect-causing substances. The EPA (US Environmental Protection Agency) labels these and other toxins as "PBT's" for Persistent Bioaccumulative Toxins. In fact, in some developed countries, one World Health Organization Study found that breast milk contains up to seventeen times the levels of pesticides and dioxins considered safe for adults. Moreover, some experts suggest that in the first six months, infants receive from breast milk as much dioxin as they should receive in a lifetime. And, as many as twenty-five percent of mothers in the United States have breast milk too high in PCB's, etc. to even pass the standards for infant formula. Furthermore, one North Carolina study involving over 800 mothers suggests that toxins passed from a mother's milk to her infant are the highest for the mother's first infant and during the first month of breastfeeding the infant. Thus, pregnancy and breastfeeding pull multiple fats, nutrients and elements from a woman's body, which are then used to build the baby. Unfortunately, these elements include toxins and become part of the baby's bones and nerves, thus carrying with it, the potential for birth defects.

In addition, not only do the various toxins passed through breast milk harm the baby, but also, if the toxins remain within the woman's system, they harm her as well. For instance, it has been proven that a woman who breastfeeds has a lower incidence of breast and other cancers, because breastfeeding is said to remove carcinogenic toxins from the woman. It has also been suggested that toxins also contribute to infertility. Many of these "PBT's" are considered estrogen disruptors and can contribute to infertility. A woman may have an especially high incidence of toxins if exposed harmful toxins in the workplace, or by exposure to hazardous material, through food contamination, or by taking various toxic drugs. Lead, another harmful substance, accumulates in a woman's bones. One Australian and EPA joint study indicates a significant increase in the mobilization of this lead during breastfeeding. This lead removal via lactation was so powerful that lead stores in the woman's bones etc. were removed from childhood ingestion in these subjects that emigrated from Eastern Europe. This could be proven because Australian lead has a different atomic weight that E.Europe lead. Many toxins can only be removed through lactation, they would accumulate throughout her lifetime causing her harm.

Studies show the levels of toxins strikingly decrease over later months of breastfeeding and decrease even more, with later babies. In other words, most women pass on these harmful toxins to their first baby during the first months of breastfeeding. Thus, there is a need for inducing lactation in a woman who is not pregnant, or may even never become pregnant, for the purpose of cleansing her body, and more specifically, for the purpose of reducing her incidence of breast and other cancers and increasing her fertility. There is also a need for inducing lactation in a woman prior to pregnancy and thereby, preventing toxins from being passed to her child once born. There is also a need for stimulating lactation in a woman who has just delivered a baby and for reducing those toxins that would normally enter the baby through breast milk by use of a superior lactation-induction mechanism.

Lactation induction is achieved by a variety of methods, and is traditionally achieved for the exclusive purpose of breastfeeding a newborn infant. If a woman desires to induce lactation, and she is not pregnant, she must mimic in her body the natural changes that would occur in a woman who recently delivered a baby. Specifically, production of milk in a woman is a result of pituitary gland stimulation in her brain. Such stimulation causes the release of two hormones: prolactin and oxytocin. Prolactin tells the woman's body to begin producing milk, while oxytocin enables the release of milk from the alveoli of her breast. The sudden release of milk is known as the let-down reflex or milk-ejection reflex. The presence of maternal and psychological factors also influences lactation, such that a woman's let-down reflex often responds to the presence of a suckling infant. In sum, inducing lactation in women who are not or have never been pregnant would take more effort. Pregnancy causes development of breast tissue preparatory to lactation. First choice would be physical stimulation alone for a number of weeks. Failing that, hormone administration described herein might be necessary. This would be worth it in a woman such as a high risk for future breast cancer patient. This hormone drug administering would mimic the hormone fluctuations naturally occuring in a woman who recently delivered a baby, and by physically stimulating the breast.

Before a woman even starts this process she needs rigorous tests to make sure she doesn't already have cancer. This would include doctors exam, Pap smear, mammogram, blood tests, colonoscopy. etc. These tests are necessary because many cancers are stimulated by hormones. Breast tumors are tested by pathologists to see if they are "Estrogen Receptor Positive" or not, with a rating score. Also, any woman who has ever had any cancer, likely should not undergo this process due to the risk of stimulating existing stray cancer cells with changing hormone levels. Typically, a one centimeter tumor sheds a million cancer "seed" cells per day capable of starting new tumors. The invention is a process where carcinogenic toxins are removed before cancer or related diseases even start. Testing of this process will determine how often it needs to be repeated (every 10+ or 5 years etc.)

As mentioned above, a common way to induce and achieve lactation in either recently pregnant women, or in women who have never been pregnant, is through use of mechanical breast pumps that stimulates milk expression. Unfortunately, there are numerous shortcomings with inducing lactation using presently available breast pumps either exclusively, or coupled with lactation-inducing drugs. First, with respect to breast pumps, most consist of cold, unfeeling mechanical devices that do not effectively lead to pituitary and hormonal response. Present breast pumps are generally based on the use of a Suction cup structure that fits over the breast. These suction cups are structurally dissimilar to a baby's mouth, which fits over the breast more naturally. A pump more closely paralleling a baby's mouth would result in more effective milk production because a baby's mouth can create a deeper compression than the surfaces of suction cups of current pumps. Present devices, such as found in Larsson's U.S. Pat. No. 5,049,126 attempt to create better nipple stimulation, yet fail to achieve compression similar to a baby's mouth.

Moreover, milk production is hindered by pain; or even by the woman's state of mind if she is, perhaps, embarrassed. Use of breast pumps are often abrasive and also are embarrassing. Breast pumps also tend to inhibit the let-down reflex. Additionally, use of currently available breast pumps tends to reduce the number of months a woman lactates. Working women tend to use breast pumps more frequently than non-working women and also have been found to discontinue lactation after a few months because of discomfort and other reasons.

Thus, there is a need for a method of inducing and achieving lactation for the purpose of removing toxins from a woman's body, and more particularly, there is a need for a method that includes using a breast pump to stimulate lactation, which more closely mimics a baby so that efficient, optimal and painless milk expression is achieved.

SUMMARY AND OBJECTS OF THE INVENTION

Some embodiments of the present invention provide a method for inducing and achieving lactation for the purpose of removing toxins from a woman's body.

In a preferred embodiment, lactation is induced and achieved for the exclusive purpose of removing harmful toxins from a woman's body, and for the purpose of preventing those toxins from being passed on to her children. In the preferred embodiment, and for a non-pregnant woman, toxins are removed by: stimulating the areolas of the woman's breast; administering hormones to the woman to induce lactation; enabling the woman to lactate a sufficient quantity to decrease the level of toxins found her in her body; and then monitoring the level of toxin until the toxins reach a less harmful level. Stimulation of the areolas is accomplished through use of a breast pump that physically mimics a baby. To induce lactation for a woman who recently delivered a baby, only physical stimulation is required.

Inducing lactation in women who have not been pregnant may require the additional step of administering hormone drugs mimicking the hormone fluctuations naturally occurring in women who recently delivered a baby, and by physically stimulation of the breast. In the preferred embodiment, the drugs should represent the natural hormones occurring in pregnant women that ultimately lead to milk production and consequently, toxin removal. Specifically, lactation may be induced in a nonpregnant woman by administering an estrogen-type substance to a woman that helps the woman simulate in her own body the high-estrogen state found in a pregnant woman. Then, the estrogen-type substance is abruptly withdrawn. This mimics the rapid hormonal change occurring in a pregnant woman following delivery of a baby. Finally, a prolactin-enhancing drug is administered to the woman to stimulate production of milk.

Physical stimulation to induce lactation for the purpose of toxin removal in the preferred embodiment, for both never been pregnant and previously pregnant women, is accomplished by using a breast pump created in the form of a baby mannequin. That is, physical stimulation occurs by using a baby mannequin-breast pump that looks, feels, sounds, acts and suckles similarly to a real infant. This mannequin-pump enables optimal milk expression because, as mentioned previously, milk expression is often dependent on psychological factors for the mother. In fact, though lactation is mainly an involuntary response to stimulus and hormones as described above, there is a significant role played by a woman's psychology, or in other words, by her state of mind. Specifically, the let-down reflex, which activates milk flow is triggered by the sight or sound of a baby. In fact, many women while using breast pumps, in order to activate milk flow must first concentrate on their baby, hear the sound of a baby, or bring a picture of their baby to view in conjunction with use of the breast pump in order to trigger lactation. Further, because breast pumps generally use suction cups, which are structurally dissimilar to an infant's mouth, pain can result and hinder optimal milk expression. Thus, use of the baby mannequin-breast pump to trigger lactation allows for optimal conditions for toxin removal, both physically and psychologically.

Consequently, in the preferred embodiment, for toxin removal to be achieved, the woman should follow the above-outline procedure. However, with respect to the baby mannequin-breast pump specifically, this device should be used four or more times per day, for ten minutes at a time. Such use sends signals to the pituitary gland to start milk production and takes four to ten days to achieve milk production.

Detailed use of the baby mannequin-breast pump in the preferred embodiment is detailed by the following. The mouth of the baby mannequin-breast pump creates the vacuum required to suckle breast milk from the woman's breast. The mouth and tongue move mechanically in a contraction-and-dilation-type action to take the woman's breast into the mouth of the baby mannequin-breast pump. This contraction-and-dilation-type action creates what is known as the "latch on" to the woman's breast and enables milk expression. A tube is connected at a first end to a mouth-like vacuum, and at a second end, to a storage chamber. Milk is drawn from the woman through the tube via the mouth and tongue and is stored within the storage chamber. Alternatively, to make cleaning of the baby mannequin-breast pump easier and milk removal easier, the tube can also connect to a flexible bag with measurement lines on the bag that measure the amount of milk (or toxins) being removed. The bag can then be placed inside a piston-sealed vacuum chamber or other variable or fixed chamber. In the preferred embodiment, the storage chamber and mouth (i.e., the vacuum-related components) are powered either by movement of the mannequin's limbs, or by manual control from the mother. However, they are not limited to these means. Moreover, manual control by the mother may entail the mother's foot activating the vacuum by pressing a pump at the end of the hose; the pump being connected to the storage chamber and mouth.

Also in the preferred embodiment, power for the toxin-removing baby mannequin-breast pump may be provided by use of electricity, solar electric power, water pressure, mechanical fall of a weight, stored spring tension, stored vacuum flow, hospital-type remote driven vacuum lines, or other means of delivering energy to a device. The contraction-and-dilation-type action of the mannequin's mouth and tongue also may be powered by vacuum or pneumatic pressure, electro-mechanical, or other means. To further enhance the psychological component of milk expression, a Central Processing Unit (hereinafter "CPU") may be placed within the mannequin, or even remotely attached using wires or other signals, such as light or radio waves, to control all aforementioned functions of the mannequin. The CPU enables the ability for the baby mannequin-breast pump to open and close its eyes, make lifelike baby sounds, or make other head and body movements that foster psychological feelings contributing to the let-down reflex. The CPU may also enable lifelike "cries" to be made by the baby mannequin-breast pump and, which may also be set by alarm to mimic a baby's cry for feeding. This alarm can be timed to be in sync with the mother's milk output and to trigger a psychological response that facilitates milk flow. The CPU may even be controlled to make satisfaction sounds similarly to a live baby in response to milk output.

Other features of the toxin-removing baby mannequin-breast pump found in the preferred embodiment include, but are not limited to: enabling the mannequin's face and head to generate heat so that the mother may feel the warmth of the mannequin while lactating, further fostering optimal milk expression and toxin removal; having a milk flow sensor and valve within the mannequin that mimics what a live infant does while nursing, which is pausing and continuing until more milk lets down and the milk ducts empty; having the milk flow sensor and valves measure the total milk and toxin flow for that feeding and using such information to measure toxin level; also having the milk flow sensor and valves indicate to the CPU when lactation is no longer needed; and finally, having the storage chamber equipped to serve as a cooling or re-heating device to store the milk for later feedings of the baby if so desired.

In some embodiments, lactation is induced and achieved for toxin removal through use of only the head of the baby mannequin-breast, thus creating a more portable unit than is present with the entire baby mannequin-breast pump described above.

In other embodiments, the toxin-removing baby mannequin-breast pump could be manufactured to be easily adaptable to heads of dolls or the like, and made to work similarly to the aforementioned baby mannequin-breast pump.

Alternatively, in even other embodiments, the head of toxin-removing the baby mannequin-breast pump could be made to easily adapt to presently available breast pumps, wherein the head replaces the suction cup end of presently available breast pumps. The easiest embodiment would be to cut away the mouth of a baby like doll and mount a current suction cup device from a breast pump where the mouth was. This would accomplish some of the psychological advantages of the invention although not have the mechanical improvements above.

In even other embodiments, the toxin-removing baby mannequin-breast pump could be used in conjunction with some type of media element (i.e., video tape, television show, virtual reality mechanism, sound recording, etc.), which presents sounds, or sights that would facilitate milk expression through psychological means. Specifically, such media element could be of a baby cooing, hypnosis, or other means that might aid in the psychological component of lactation.

In some embodiments, a woman can learn what helps her create optimal milk expression, and therefore optimal toxin removal, by making the mannequin in a way that allows for biofeedback. In essence, she could use the mannequin's biofeedback features to tune in to what feelings help her achieve optimal milk expression. The biofeedback features could entail measuring galvanic skin response, electromyleograph, electroencephlograph, or other similar measurements. Also, electronic nerve stimulation and other types of physical and medical therapy could be used to induce lactation and one way to use biofeedback to train the woman to lactate. The goal is that in a few sessions with the mannequin, the woman could learn what triggers lactation.

In some embodiments, where the woman has recently delivered a baby and wants to prevent the baby from receiving toxins passed through breast milk, the mother could use the baby mannequin-breast pump in between feeding times for the baby, or along with formula supplementation for the baby, so that toxin passage is minimized.

In some embodiments, lactation is induced and achieved for the purpose of increasing a woman's fertility.

In other embodiments, lactation is induced and achieved for the purpose of fostering weight loss in a woman.

In other embodiments, lactation is induced and achieved for the purpose or cleansing a woman's body and thereby, lowering her incidence of breast and other cancers.

Accordingly, it is an object of some embodiments of the present invention to provide a method for inducing and achieving lactation for the purpose of cleansing a woman's body, removing toxins from the woman's body, lowering her incidence of breast and other cancers, preventing subsequently-born children from consuming toxins, increasing the woman's fertility and fostering her weight loss.

Another object of some embodiments of the present invention is to induce and achieve lactation for the purpose of toxin removal by providing a baby mannequin-breast pump that looks, feels, sounds, acts and suckles similarly to a real infant so that optimal, efficient and painless milk expression and toxin removal is achieved.

These and other objects of the present invention will become more fully apparent from the following description, drawings, and claims. Other objects will likewise become apparent from the practice of the invention as set forth hereafter.

BRIEF DESCRIPTION OF THE DRAWINGS

The foregoing and other objects and features of the present invention will become more fully apparent from the accompanying drawing when considered in conjunction with the following description and appended claims. Although the drawing depicts only a typical embodiment of the invention and is thus, not to be deemed limiting of the invention's scope, the accompanying drawing helps explain the invention in added detail.

DETAILED DESCRIPTION OF THE INVENTION

Figure 1:
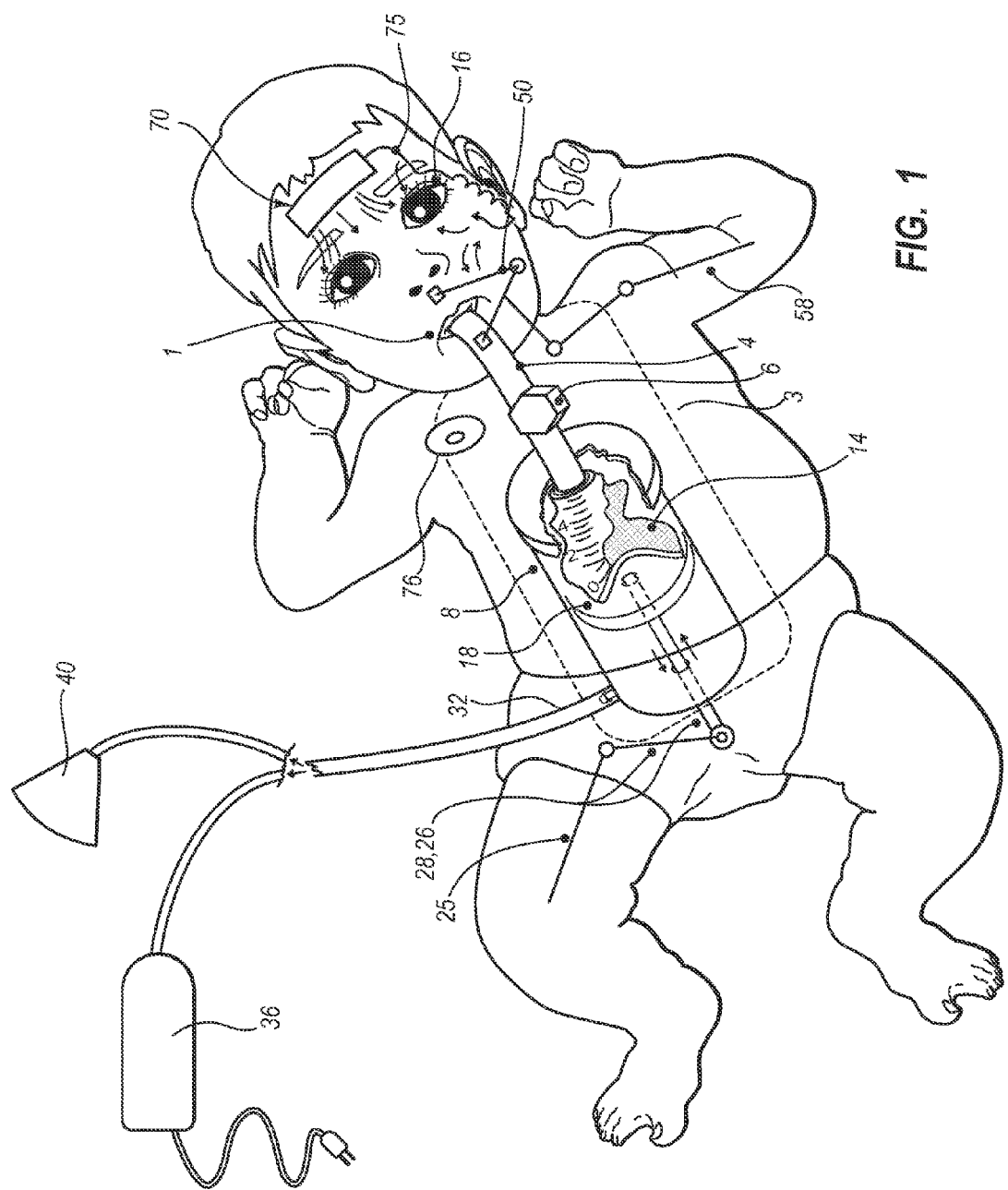
FIG. 1 depicts one perspective of the preferred embodiment of the present invention and displays a toxin-removing baby mannequin-breast pump.

It is emphasized that the present invention, as illustrated in the figure and description herein, can be embodied in other forms. Thus, neither the drawing nor the following more detailed description of the various embodiments of the system and method of the present invention limited the scope of the invention. The drawing and detailed description are merely representative of the particular embodiment of the invention; the substantive scope of the present invention is limited only by the appended claims. The various embodiments of the invention will best be understood by reference to the drawing, wherein like elements are designated by like alphanumeric characters throughout.

With reference now to the accompanying drawing, FIG. 1 depicts the toxin-removing baby mannequin-breast pump previously described in the preferred embodiment. In this depiction, toxins are removed via lactation induction in either a nonpregnant, or in a recently pregnant woman. In the instance of the non-pregnant woman, toxins are removed by: stimulating the areolas of the woman's breast; administering hormones to the woman to induce lactation; enabling the woman to lactate a sufficient quantity to decrease the level of toxins found her in her body; and then monitoring the level of toxin until the toxins reach a less harmful level.

Administering hormones to induce lactation entails: administering an estrogen-type substance to the woman in an amount necessary to simulate the high-estrogen state found in a pregnant mammal; abruptly withdrawing the estrogen-type substance to mimic the rapid hormonal changes occurring in a pregnant woman following the delivery of a baby; and administering a prolactin-enhancing drug to the woman.

Stimulation of the areolas is accomplished through use of a breast pump depicted in FIG. 1, which physically mimics a baby and as depicted. To induce lactation for a woman who recently delivered a baby, only physical stimulation is required.

Specifically, in FIG. 1, the mouth and tongue (12) of the baby mannequin-breast pump create a vacuum (42) required for pulling breast milk and toxins from the woman's breast. The mouth and tongue (12) move mechanically in a contraction-and-dilation-type action to take the woman's breast into the mouth and tongue (12) of the baby mannequin-breast pump. This contraction-and-dilation-type action creates what is known as the "latch on" to the woman's breast and enables milk expression and ultimately, toxin removal. A tube (36) is connected at a first end (38) to the mouth and tongue (12), and at a second end (40), to a storage chamber (14). Milk is drawn from the woman through the tube (36) via the mouth and tongue (12) and is then stored within the storage chamber (14). Alternatively, to make cleaning of the baby mannequin-breast pump easier and toxin removal easier, the tube (36) can also lead to a flexible bag (16) with measurement lines on the flexible bag (16) that serve to measure the amount of milk (or toxins) being removed. The flexible bag (16) can then be placed inside a piston-sealed vacuum chamber (18) or other variable or fixed chamber. In the preferred embodiment, the storage chamber (14) and mouth and tongue (12) (i.e., the vacuum-related components) are powered either by movement of the mannequin's legs (20) or arms (22), or by manual control by the mother. However, they are not limited to these means. Moreover, manual control by the mother may entail the mother's foot activating the vacuum caused by the mouth and tongue (12) by pressing a vacuum pump (24) at the end of a hose (26); the vacuum pump (24) being connected to the storage chamber (14) and mouth and tongue (12).

Also in the preferred embodiment, power for the toxin-removing baby mannequin-breast pump may be provided by use of electricity, solar electric power, water pressure, mechanical fall of a weight, stored spring tension, stored vacuum flow, hospital-type remote driven vacuum lines, or other means of delivering energy to a device. The contraction-and-dilation-type action of the mannequin's mouth and tongue (12) also may be powered by vacuum or pneumatic pressure, electro-mechanical, or other means. To further enhance the psychological component of milk expression, a Central Processing Unit (hereinafter "CPU") (28) may be placed within the mannequin, or even remotely attached using wires or other signals, such as light or radio waves, to control all aforementioned functions of the mannequin. The CPU (28) enables the ability for the baby mannequin-breast pump to open and close its eyes (16), make lifelike baby sounds, or make other head and body movements that foster psychological feelings contributing to the let-down reflex. The CPU (28) may also enable lifelike "cries" to be made by the baby mannequin-breast pump and which may also be set by alarm to mimic a baby's cry for feeding. This alarm can be timed to be in sync with the mother's milk output and to trigger a psychological response that facilitates milk flow. The CPU (28) can even be controlled to make satisfaction sounds similarly to a live baby in response to milk output.

Other features of the toxin-removing baby mannequin-breast pump found in the preferred embodiment include, but are not limited to: enabling the mannequin's face and head (32) to generate heat so that the mother may feel the warmth of the mannequin while lactating, further fostering optimal milk expression; having a milk flow sensor and valve (34) within the mannequin that mimics what a live infant does while nursing, which is pausing and continuing until more milk lets down and the milk ducts empty; having the milk flow sensor and valves (34) measure the total milk and toxin flow for that feeding and using such information to measure toxin level; also having the milk flow sensor and valves (34) indicate to the CPU when lactation is no longer needed; and finally, having the storage chamber (14) equipped to serve as a cooling or re-heating device to store the milk for later feedings of the baby if so desired.

What is claimed is:

1. A method for reducing carcinogenic toxin from a body comprising the steps of:
   stimulating a mammal's areolas to induce lactation; and
   lactating a sufficient quantity to decrease the toxins in said mammal, until reaching a less harmful level, comprising:
   employing a device that further facilitates expression of a substance from a breast of said mammal, said device comprising:
   a lactation-inducing baby mannequin;
   means for producing a vacuum;
   a tube having a first end and a second end, wherein said first end of said tube is connected to said vacuum; and
   a storage chamber that is connected to said second end of said tube, wherein said storage chamber receives said substance drawn by said vacuum from said breast of said mammal through said tube.

2. A method as described in claim 1, wherein said device is controlled by a central processing unit, wherein said central processing unit controls and creates said vacuum and measures the output of said substance from said breast.

3. A method as described in claim 1, wherein said lactation-inducing baby mannequin further comprises:
   a mouth for receiving said breast of said mammal;
   limbs for use in operating said device;
   a body that provides said mouth and limbs and;
   a central processing unit within said body for providing function to said device.

* * * * *